United States Patent [19]

Sallet et al.

[11] Patent Number: 4,935,459

[45] Date of Patent: Jun. 19, 1990

[54] SYNTHETIC RESIN COMPOSITIONS COMPRISING FLAMEPROOFING AMOUNTS OF NITROGENOUS/HALOMETALLIC COMPOUNDS

[75] Inventors: Daniel Sallet, Serquigny; Pierre Deloy, Levallois-Perret; Valerie Mailhos-Lefievre, Paris; Pierre Poisson, Bernay, all of France

[73] Assignee: Atochem, Puteaux, France

[21] Appl. No.: 398,380

[22] Filed: Aug. 24, 1989

[30] Foreign Application Priority Data

Aug. 24, 1988 [FR] France .................. 88 11184

[51] Int. Cl.⁵ .................................. C08K 5/59
[52] U.S. Cl. ............................. 524/94; 524/93; 524/100; 524/204; 524/236; 544/225; 544/181; 548/262; 548/305; 548/306; 548/404; 548/107; 548/101; 556/64
[58] Field of Search ............ 524/94, 93, 100, 236, 524/204; 544/225, 181; 548/262, 305, 306, 404; 556/64

[56] References Cited

U.S. PATENT DOCUMENTS

| | | | |
|---|---|---|---|
| 2,028,333 | 6/1977 | Lindvay | 524/100 |
| 3,239,482 | 3/1966 | Rapp | 524/410 |
| 3,542,828 | 11/1970 | Harris | 556/64 |
| 3,705,128 | 12/1972 | Knowles | 524/97 |
| 3,879,312 | 4/1975 | Udding et al. | 556/64 |
| 4,264,364 | 4/1981 | Lippoldt | 524/204 |
| 4,359,538 | 11/1982 | Bertrand | 524/237 |
| 4,798,857 | 1/1989 | Bertelli et al. | 548/404 |

FOREIGN PATENT DOCUMENTS 273458 7/1988 European Pat. Off. .
7402361 8/1975 Netherlands .

OTHER PUBLICATIONS

N. K. Jha and S. S. A. Rizvi-J. Inorg. Nucl. Chem. 34, No. 9 (Sep. 1972), 2953-2955.
R. D. Whealy and R. L. Yeakley-J. Inorg. Nuclear Chem. 25 365-368 (1963).

*Primary Examiner*—Veronica P. Hoke
*Attorney, Agent, or Firm*—Burns, Doane, Swecker & Mathis

[57] ABSTRACT

Flameproofed compositions of matter include an organic synthetic resin and, as a flame retardant therefor, an effective flameproofing amount of specified nitrogenous/halometallic compounds, certain of which are per se novel.

27 Claims, No Drawings

SYNTHETIC RESIN COMPOSITIONS COMPRISING FLAMEPROOFING AMOUNTS OF NITROGENOUS/HALOMETALLIC COMPOUNDS

BACKGROUND OF THE INVENTION

1. Field of the Invention

The present invention relates to novel compounds for the flameproofing of synthetic resins, and, more especially, to novel flameproofing compounds comprising at least one organometallic salt containing nitrogenous cationic moieties and halometallic anionic moieties.

2. Description of the Prior Art

It is known to this art that, for many applications, synthetic polymeric materials are required which have improved flame- or fireproofing properties.

Thus, various halogenated organic compounds, such as chlorinated paraffins, polybromodiphenyl ethers, and the like, are currently used for such purpose.

Inorganic salts such as $(NH_4)_2TiF_6$ for the fireproofing of synthetic resins such as polystyrene, polypropylene or ABS resins are also known to this art, as described in U.S. Pat. No. 3,643,311.

To provide a sufficient level of effectiveness, it is necessary to use these organic or inorganic compounds in combination with metal oxides such as antimony trioxide or bismuth trioxide.

However, this presents the disadvantage of generally having to employ high percentages of such additives, which may be up to 30% to 40% of the total weight of the composition, and whose nature is such that they adversely affect the mechanical properties of the fireproofed materials.

SUMMARY OF THE INVENTION

Accordingly, a major object of the present invention is the provision of novel organometallic flame retardants for synthetic resins, which organometallic flame retardants are effective at lower dosages and comprise nitrogenous cationic moieties and halometallic anionic moieties, having the following general formula (I):

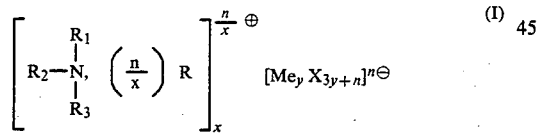

in which R, $R_1$, $R_2$ and $R_3$, which may be identical or different, are each a hydrogen atom, a liner or branched chain aliphatic hydrocarbon radical optionally substituted by one or more halogen atoms and containing up to 12 carbon atoms, a cycloaliphatic radical, or a phenyl radical or phenyl radical substituted by one or more halogen atoms, amino groups, or linear or branched chain aliphatic radicals containing up to 6 carbon atoms with the proviso that $R_1$, $R_2$ and $R_3$ may together form, with the nitrogen atom from which they depend, an aromatic heterocyclic ring member, or substituted such ring member bearing one or more linear or branched chain aliphatic radicals containing up to 6 carbon atoms or halogen atom substituents, with the further proviso that $R_2$ and $R_3$ may together form, with the nitrogen atom from which they depend and a divalent radical (Y), a heterocyclic ring member containing from 2 to 10 carbon atoms and having the formula:

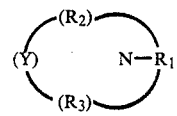

wherein (Y) is a valence bond, $>N-H$, $-O-$, $-S-$,

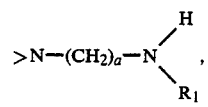

with a ranging from 2 to 6, and $R_1$ is as defined above, with the further proviso that $R_3$ may itself be a nitrogenous heterocyclic ring member, or substituted such heterocycle bearing one or more halogen atom, amino group, linear or branched chain aliphatic radical containing up to 10 carbon atoms, phenyl radical or amino residue substituents of the formula:

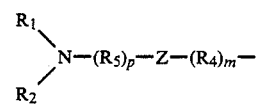

wherein $R_1$ and $R_2$ are as defined above, and $R_4$ and $R_5$, which may be identical or different, are each a divalent nitrogenous heterocyclic radical or a methylene radical, Z is a single valence bond or a divalent radical selected from among the following:

$-NH-(CH_2)-bNH-$, with b ranging from 0 to 6, $-(CH_2)-_c$, with c ranging from 1 to 6, and

and p and m range from 1 to 6; Me is a metal such as arsenic(III), antimony(III) or bismuth(III); X is a halogen atom such as bromine, chlorine or iodine; and x, y and n are integers ranging from 1 to 10, with $n \geq x$.

DETAILED DESCRIPTION OF THE PREFERRED EMBODIMENTS OF THE INVENTION

More particularly according to the present invention certain haloantimonates and halobismuthates of formula (I) are per se known to this art, namely, those in which the cationic moiety is $[NH_4]_x^\oplus$, described by G. Jander, Z. Electrochim., 61, 1275 (1957) and by L. P. Pandey, J. Indian Chem. Soc., 41 (11) 771-3 (1964), or those in which the cationic moiety is an alkylammonium, alkyldiammonium, anilinium, cyclohexylammonium or piperidinium radical, which are described by R. D. Whealy and R. L. Yeakley, J. Inorg. Nucl. Chim., 25, 365-368 (1963) and by M. A. Hooper and D. W. James. Aus. J. Chem., 26, 149-12 (1973), or else a pyridinium and quinolinium radical, which are described by J. M. Stewart et al, *Inorganic Chemistry*, 13 (11) 2767 (1974).

Compounds of formula (I) are also know to this art, in which the cationic moiety is a tetraalkylammonium, which are described by G. Y. Ahlijah and M. Goldstein, *J. Chem. Soc.*, (A), 326–328 (1970).

Nonetheless, it will of course be appreciated that no such reference discloses or suggests the use of these particular compounds as flame retardants for synthetic polymeric materials.

The remaining compounds are novel and have the formula (I-a):

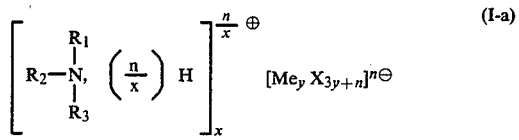

In said formula (I-a), $R_1$ and $R_2$, which may be identical or different, are each a hydrogen atom, a linear or branched chain aliphatic hydrocarbyl radical containing up to 12 carbon atoms or a phenyl radical; $R_3$ is a nitrogenous heterocyclic radical, or a C-substituted such heterocycle bearing one or more halogen atom, amino group, or linear or branched chain aliphatic radical substituents containing up to 10 carbon atoms, or phenyl radicals or amino residues of the formula $H_2N—(R_5)_p—Z(R_4)_m—$ in which $R_4$ and $R_5$, which may be identical or different, are each divalent heterocyclic radicals, Z is a divalent radical selected from among the following:

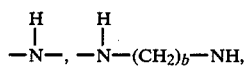

with b ranging from 0 to 6,

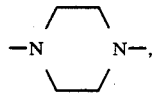

or a $—(CH_2)—_c$ radical, with c ranging from 1 to 6, when $R_5$ and $R_4$ are divalent heterocyclic radicals, and p and m range from 1 to 6, with the proviso that $R_2$ and $R_3$ may together form, with the nitrogen atom from which they depend and a divalent radical $>N—H$ or $>N—(CH_2)_a—NH_2$, with a ranging from 2 to 6, a heterocyclic ring member containing from 2 to 10 carbon atoms; and Me, X, n, x and y are as defined above.

In general, the compounds of formula (I) can be prepared according to methods which are per se known to this art. For example, the techniques described by Whealy and R. L. Yeakley (op. cit.) and by G. C. Allen and R. F. McMeeking, *Inorganica Chimica Acta*, 23, 1985-190 (1977) may be employed, which entail reacting an ammonium halide with a metal halide.

Another method entails reacting an amine with a metal halide in a hydrogen halide solution (see, for example, the article by J. M. Stewart (op. cit.)).

The compounds of formula (I-a) according to the present invention are conveniently prepared by the following techniques, similar to those outlined above.

Thus, in a first alternative embodiment, an amine is reacted with an acid hydrogen halide and then the substituted ammonium halide obtained is complexed with a metal halide in a hydrogen halide solution according to the reactions:

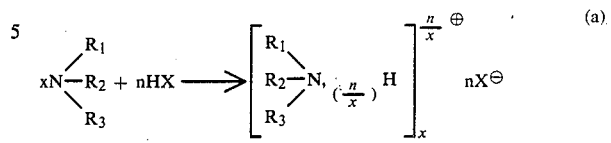

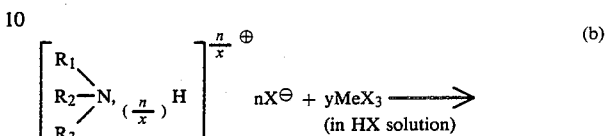

In a second alternative embodiment, an amine is reacted with the metal halide in a hydrogen halide solution containing an excess of hydrogen acid according to the reaction:

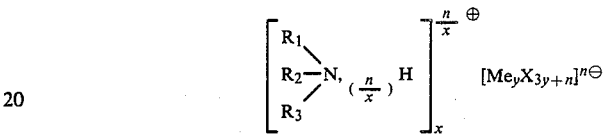

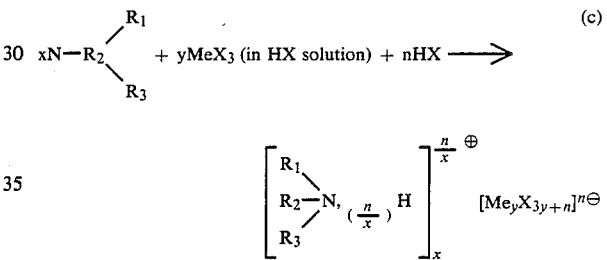

Exemplary of the amines which can thus be employed, representative are acetoguanamine, benzoguanamine, 3-amino-1,2,4-triazole, 3,5-diamino-1,2,4-triazole (guanazole), 2-aminobenzimidazole, N-aminophthalimide, N-aminotetrabromophthalimide, 2,4-diamino-6-nonyl-1,3,5-triazine, N,N'-bis(1,3,5-triazinyl-2,4,6-triamino)-1,2-ethane, N,N'-bis(1,3,5-triazinyl-2,4,6-triamino)piperazine, 1-(2-aminoethyl)piperazine, bis(2-aminoethyl)amine and piperazine.

Whichever of the alternative embodiments is involved, an aqueous solution of metal halide is employed, prepared by dissolving a metal oxide in a concentrated aqueous solution of acid hydrogen halide according to the reaction:

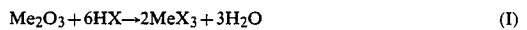

The operation is carried out using an excess of acid hydrogen halide relative to the stoichiometry of the reaction (1) of between 50% and 100% molar, preferably ranging from 70% to 80% molar (solution S).

In the first alternative embodiment, it is possible to employ a concentrated aqueous solution (or a suspension) of substituted ammonium halide, obtained by the addition of an amine to a concentrated aqueous solution of acid hydrogen halide at a concentration of from 25% to 60% by weight of acid hydrogen halide, and preferably from 35% to 50%.

The operation is preferably carried out using stoichiometric amounts of the reactants, but it is possible to employ a slight excess of acid hydrogen halide relative to the amine (reaction a).

According to this same alternative embodiment, it is also possible to employ the substituted ammonium halide as such.

The solution of substituted ammonium halide (or else the substituted ammonium halide as such) is next introduced into the metal halide solution S at a temperature of from 20° to 50° C., preferably from 30° to 40° C., over a period of time which can range from 1 to several hours, with good stirring.

With regard to the second alternative embodiment, the amine is introduced into a hydrogen halide solution of metal halide $S_1$. This solution $S_1$ is prepared by adding to the solution S the stoichiometric amount of acid hydrogen halide according to reaction (c) in the form of a concentrated aqueous solution of this acid hydrogen halide.

The addition of the amine is carried out under stirring at a temperature of from 20° to 50° C., preferably from 30° to 40° C., over a period of time which can range from 1 to several hours.

When the addition of the amine (or of the substituted ammonium halide) is completed, stirring of the reaction mixture is continued for approximately one hour at ambient temperature (approximately 20° C.).

The compounds produced generally precipitate during the addition of the amine or of the substituted ammonium halide.

Known means are used to isolate such final compounds: concentration of the solution in the event that the compound is soluble in the aqueous hydrogen halide solution, filtration, washing of the precipitation obtained with anhydrous solvents such as carboxylic acids (for example acetic or propionic acid), ketones (for example acetone or butanone), nitriles (for example acetonitrile), ethers (for example diethyl ether, tetrahydrofuran) or mixtures thereof.

The washed product is drained of liquid and then dried at about 130° C. under reduced pressure to constant weight. Advantageously, the product is ground such as to provide a powder which has a particle size of from 1 to 50 microns and preferably from 5 to 25 microns.

The products obtained are more or less yellow-colored powders.

Elemental analysis (C, H, N, metal, halogen, etc.) enables the resulting compounds to be characterized.

Among the compounds of formula (I) and (I-a) according to the invention, it is preferred to use those in which Me is bismuth and more preferably antimony, and X is bromine and chlorine, and more preferably bromine.

Among the compounds of formula (I), particularly advantageous are those in which R, $R_1$, $R_2$ and $R_3$ are hydrogen atoms. Representative such compounds are:
Triammonium hexabromoantimonate(III);
Triammonium nonabromodiantimonate(III);
Heptaammonium hexadecabromotriantimonate(III);
Diammonium pentabromobismuthate(III);
Triammonium nonachlorodiantimonate(III).

Exemplary of the compounds of formula (I) in which R, $R_1$ and $R_2$ are hydrogen atoms, and $R_3$ is a linear or branched chain aliphatic hydrocarbon radical containing up to 12 carbon atoms, a cyclohexane-derived radical or a phenyl radical, representaative are bis(n-butylammonium), bis(isobutylammonium), bis(tri-n-butylammonium), bis(anilinium) and bis(cyclohexylammonium) pentabromoantimonates(III).

It is also possible to use the compounds of formula (I) in which $R_1$, $R_2$ and $R_3$ together form, with the nitrogen atom from which they depend, an aromatic heterocyclic ring, or substituted such heterocycle bearing one or more halogen atom substituents, or linear aliphatic hydrocarbyl radicals containing up to 3 carbon atoms. Exemplary such aromatic heterocyclic rings are pyridine and derivatives thereof (for example bromo- and chloropyridines and alkylpyridines) and quinoline.

Among the compounds of formula (I) and (I-a) in which R and $R_1$ are hydrogen atoms, and $R_2$ and $R_3$ together form, with the nitrogen atom from which they depend and the (Y) radical, a heterocyclic ring containing from 2 to 6 carbon atoms and having the formula:

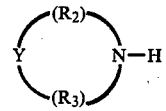

in which Y is a valence bond, H—N< or >N—(CH$_2$)$_2$—NH$_2$, representative are bis(piperidinium), piperazinium and 1-(2-ammonioethyl)piperazinium pentabromoantimonates(III), piperazinium pentabromobismuthate(III) and 1-tris(2-ammonioethyl)piperazinium dodecabromodiantimonate(III).

Also advantageously used are the compounds of formula (I) in which R, $R_1$ and $R_2$ are hydrogen atoms, $R_3$ is a nitrogenous heterocyclic radical, or substituted such heterocycle bearing one or more amino group substituents, or linear aliphatic hydrocabyl radicals containing up to 10 carbon atoms or phenyl radicals. Exemplary such nitrogenous heterocyclic rings are those comprising an s-triazine, 1,3-diazine, 1,2,4-triazolyl, benzimidazolyl and phthalimide structure.

Representative compounds comprising such heterocyclic rings are bis(malaminium), bis(benzoguanidinium), bis(acetoguanidinium) and bis(2-ammoniobenzimidazole) pentabromoantimonates(III) and tris(3-ammonio-1,2,4-triazole)hexabromoantimonate(III).

$R_3$ may also be an amino residue of the formula H$_2$N(CH$_2$)$_p$—Z—(CH$_2$)$_m$—, in which Z is a single valence bond or the >N—H group and p and m are identical and range from 1 to 3. 1,2-Diammonioethane pentabromoantimonate(III) and bis(2-ammonioethyl)ammonium hexabromoantimonate(III) are exemplary.

The incorporation of the compounds of formula (I) into compositions of matter comprising organic materials and especially synthetic resins enables their flame retardant activity to be improved.

The compounds according to the invention are advantageously incorporated in amounts ranging from 1% to 18%, preferably from 3% to 15%, and more preferably from 5% to 12% by weight relative to the resin to be fireproofed.

Exemplary of the synthetic resins which may be fireproofed using the compounds of the present invention, representative are with no limitation being implied: polyolefins, polyamides, polyesters, vinyl resins, ABS resins, epoxy resins, and the like.

The flameproofed compositions are formulated by incorporating the compounds according to the invention by blending the finely divided compounds into the molten resin. Any blending apparatus which ensures good dispersion may therefore be suitable, and in particular blenders of the Buss type.

The extrusion conditions must be suitable to provide a good dispersion of the compounds, and any such process is well known to this art.

The resulting mixture is granulated. The granules can be injection- or compression-molded at suitable temperatures into standardized test specimens for performing the UL94 fire reaction test according to NF Standard T 51072, for measuring the oxygen index according to NF Standard T 51071 and the Izod impact strength according to ISO Standard 180.

A simple technique for carrying out the operation comprises mixing, in the presence or absence of a paraffin oil, the polymer granules and the compounds of formula (I) or (I-a) in finely powdered form, in a mixer of the Turbula type, and in charging a suitable blender with this mixture.

The compounds of formula (I) or (I-a) can also be charged into an extruder by means of a metering device of the Soder type.

In addition to the fireproofing additive, the synthetic resin compositions of this invention may also contain other additives and adjuvants such as pigments, colorants, UV-stabilizers, mold-release agents, stabilizers against thermal decomposition, and fillers. These compositions may also contain glass fibers for the purpose of improving the rigidity of the synthetic resin.

In order to further illustrate the present invention and the advantages thereof, the following specific examples are given, it being understood that same are intended only as illustrative and in nowise limitative.

EXAMPLE 1

Preparation of piperazinium pentabromoantimonate(III)

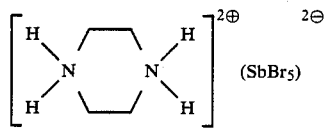

1.7 liters of a 48% strength solution of hydrobromic acid (15.3 moles of HBr) were introduced at 23° C. into a 3-liter reactor equipped with an anchor stirrer, and 437.25 g of $Sb_2O_3$ (1.5 moles) were then introduced over approximately 30 minutes in small portions and with vigorous stirring.

A clear solution was obtained, to which 743.4 g of piperazinium dibromide were added over 3 hours with vigorous stirring. The reaction was exothermic and the temperature rapidly increased to about 30°–35° C., with temperature was maintained throughout the addition period. A yellow precipitate was rapidly formed.

When the addition was completed, the suspension was maintained vigorously stirred for one hour, while the reaction mixture was cooled such as to provide a temperature in the region of 20° C.

The precipitate was filtered off and then washed with glacial acetic acid and was dried under reduced pressure at 130° C. to a constant weight.

A yellow powder was obtained.

| Elemental analysis: | | | | | |
|---|---|---|---|---|---|
| | C | H | N | Sb | Br |
| % Calculated | 7.88 | 1.65 | 4.59 | 19.97 | 65.55 |
| % Found | 7.86 | 1.8 | 4.51 | 20.3 | 61.45 |

EXAMPLE 2

Preparation of tris(piperazinium) dodecabromodibismuthate(III)

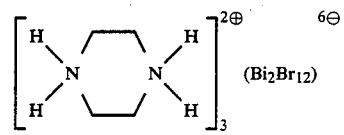

This compound was prepared according to the procedure of Example 1 by introducing 743.5 g of piperazinium dibromide (3 moles) into 2.25 liters of a 48% strength solution of hydrobromic acid containing 898 g of $BiBr_3$ (2 moles).

The subsequent processing was as in Example 1.

The compound precipitated during the addition of piperazinium dibromide.

The precipitate obtained was filtered off and then washed with glacial acetic acid and then with isopropanol.

It was dried under reduced pressure at 130° C. to a constant weight.

A yellow powder was obtained.

| Elemental analysis: | | | | |
|---|---|---|---|---|
| | C | H | N | Bi |
| % Calculated | 8.77 | 2.19 | 5.12 | 25.46 |
| % Found | 8.6 | 2.15 | 4.77 | 24.3 |

EXAMPLE 3

Preparation of bis(melaminium) pentabromoantimonate(III)

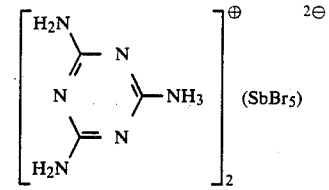

223 ml of a 48% strength solution of hydrobromic acid, namely, 2 moles of HBr, were added to a hydrogen bromide solution of antimony tribromide, prepared as in Example 1 and containing 361.45 g of antimony tribromide (1 mole).

252 g of melamine (2 moles) were added to this solution over 2 hours with vigorous stirring.

A yellow precipitate was rapidly formed. The temperature was maintained at about 30°–35° C. throughout the addition period, and then, when the addition was completed, the material was cooled to about 20° C., still with vigorous stirring.

The material was filtered off, and the resulting filter cake was then washed with glacial acetic acid.

It was dried under reduced pressure at 130° C. to a constant weight.

A pale yellow powder was obtained.

| Elemental analysis: $C_6H_{14}N_{12}SbBr_5$ (molecular weight: 775.25) | | | | | |
|---|---|---|---|---|---|
| | C | H | N | Br | Sb |
| % Calculated | 9.29 | 1.81 | 21.67 | 51.53 | 15.70 |
| % Found | 9.09 | 1.57 | 21 | 50.35 | 16.27 |

EXAMPLE 4

Preparation of bis(benzoquanaminium) pentabromoantimonate(III)

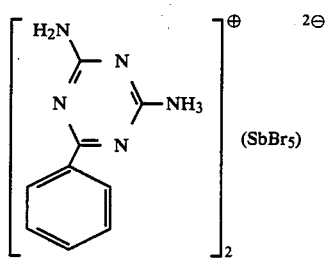

The operation was carried out as in example 3, but with the malamine replaced with 374 g of benzoquanamine (2 moles).

The product obtained was a yellow powder.

| Elemental analysis: | | | | | |
|---|---|---|---|---|---|
| | C | H | N | Br | Sb |
| % Calculated | 24.08 | 2.25 | 15.6 | 44.50 | 13.56 |
| % Found | 24 | 2.15 | 15.6 | 46.3 | 11.3 |

EXAMPLE 5

Preparation of bis(ammonio-2-benzimidazole)pentabromoantimonate(III)

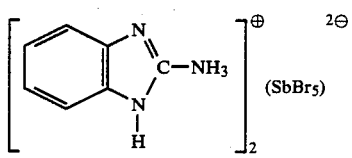

The operation was carried out as in Example 3, but with the melamine replaced with 266 g of N-aminobenzimidazole (2 moles).

The product obtained was a violet-grey powder.

| Elemental analysis: | | | | | |
|---|---|---|---|---|---|
| | C | H | N | Br | Sb |
| % Calculated | 21.3 | 2 | 10.64 | 50.6 | 15.42 |
| % Found | 21.9 | 1.52 | 10.4 | 50.15 | 15.2 |

EXAMPLE 6

Preparation of tris(3-ammonio-1,2,4-triazole) hexabromoantimonate(III)

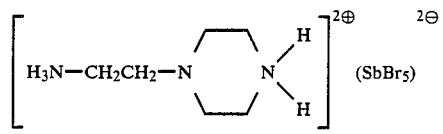

The operation was carried out as in Example 3, but with the melamine replaced with 252 g of 3-amino-1,2,4-triazole (3 moles) and using 334.5 ml of a 48% strength solution of hydrobromic acid (3 moles of HBr) instead of 223 ml.

When the addition was completed, the solution obtained was partially concentrated and was then filtered. The subsequent processing was as above.

The product obtained was in the form of a pale-yellow powder which began to soften at about 50° C.

| Elemental analysis: | | | | | |
|---|---|---|---|---|---|
| | C | H | N | Br | Sb |
| % Calculated | 8.41 | 1.77 | 19.63 | 56 | 14.22 |
| % Found | 8.3 | 1.75 | 20 | 55.9 | 14.7 |

EXAMPLE 7

Preparation of 1-(2ammonioethyl)piperaziniumpentabromoantimonate(III)

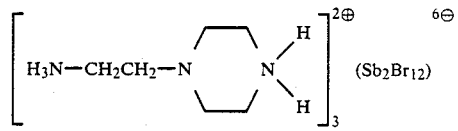

The operation was carried out as in Example 3, but with the melamine replaced with 129 g of 2-aminoethylpiperazine (1 mole).

The product obtained was a yellow powder.

| Elemental analysis: | | | | | |
|---|---|---|---|---|---|
| | C | H | N | Br | Sb |
| % Calculated | 11.04 | 2.31 | 6.44 | 61.22 | 18.66 |
| % Found | 9.74 | 2.48 | 5.69 | 61.3 | 16.5 |

EXAMPLE 8

Preparation of 1-tris(2-ammonioethyl)piperazinium dodecabromodiantimonate(III)

$$\left[ H_3N-CH_2CH_2-N\underset{\diagdown}{\overset{\diagup}{\bigcirc}}N\underset{H}{\overset{H}{\diagdown}} \right]_3^{2\oplus} \quad 6\ominus$$
$$(Sb_2Br_{12})$$

The operation was carried out as in Example 3, but with the melamine replaced with 193.5 g of 2-aminoethylpiperazine (1.5 mole) and using 334.5 ml of a 48% strength solution of hydrobromic acid (3 moles of HBr) instead of 223 ml.

The product obtained was a yellow powder.

| Elemental analysis: | | | | | |
|---|---|---|---|---|---|
| | C | H | N | Br | Sb |
| % Calculated | 13.54 | 2.84 | 7.89 | 60.07 | 15.26 |
| % Found | 10.88 | 2.57 | 6.16 | 63 | 14.77 |

EXAMPLE 9

Preparation of bis(2-ammonioethyl)ammonium hexabromoantimonate(III)

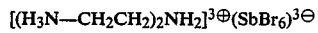

The operation was carried out as in Example 3, but with the melamine replaced with 103 g of bis(2-aminoethyl)amine (1 mole) and using 334.5 ml of a 48% strength solution of hydrobromic acid (3 moles of HBr) instead of 223 ml.

The product obtained was a yellow powder.

| Elemental analysis: | | | | | |
|---|---|---|---|---|---|
| | C | H | N | Br | Sb |
| % Calculated | 6.78 | 2.26 | 5.94 | 17.21 | 67.76 |
| % Found | 7.15 | 2.35 | 6.3 | 18.9 | 67.9 |

EXAMPLE 10

Granules of polypropylene having a density=0.905 g/cm$^3$ and a melt index of 5 (2.16 kg load at 230° C.) were extruded on a Buss blender model PR 46, in which the average temperature was 200°–210° C.

The granules produced were injection-molded into standardized test specimens which were used to perform the UL 94 test according to NF Standard T 51072 (vertical specimen), the measurement of the oxygen index (NF Standard T 51071) and the measurement of Izod impact according to ISO Standard 180 (notched specimen).

EXAMPLE 11

The following materials were mixed (Turbula mixer):
(i) 8,980 g of polypropylene granules;
(ii) 20 g of a liquid paraffin, pharmaceutical grade;
(iii) 1,000 g of triammonium hexabromoantimonate(III).

This mixture was charged into a Buss blender model PR 46 in which the average temperature was 200° C.

The granules produced were injection-molded into standardized test specimens on which the UL 94 test, the measurement of the oxygen index and of the Izod impact were carried out.

EXAMPLE 12

The procedure of Example 11 was repeated, except that the triammonium hexabromoantimonate(III) was replaced with the same amount by weight of triammonium nonabromodiantimonate(III).

EXAMPLE 13

The procedure of Example 11 was repeated, except that the triammonium hexabromoantiomonate(III) was replaced with half of its amount of heptaammonium hexadecabromotriantimonate(III).

EXAMPLES 14 AND 15

The procedure of Example 13 was repeated, except that different amounts of heptammonium hexadecabromotriantimonate(III) were employed.

EXAMPLE 16

The procedure of Example 11 was repeated, except that the triammonium hexabromoantimonate(III) was replaced with the same amount by weight of diammonium pentabromobismuthate(III).

EXAMPLE 17 TO 25

The procedure of Example 11 was repeated, except that the triammonium hexabromoantimonte(III) was replaced with the same amount by weight of the following compounds:

EXAMPLE 17 bis(melaminium) pentabromoantimonate(III);

EXAMPLE 18 bis(piperidinium) pentabromoantimonate(III);

EXAMPLE 19 bis(pieridinium) pentachloroantimonate(III);

EXAMPLE 20 bis(anilinium) pentabromoantimonate(III);

EXAMPLE 21 piperazinium pentabromoantimonate(III);

EXAMPLE 22

1-(2-ammonioethyl)piperazinium pentabromoantimonate(III);

EXAMPLE 23

1-tris(2-ammonioethyl)piperazinium dodecabromodiantimonate(III);

EXAMPLE 24

1,2-diammonioethane pentabromoantimonate(III);

EXAMPLE 25 tris(piperzinium)dodecabromodibismuthate(III).

EXAMPLE 26

This example, in which commercial products currently employed to improve the flameproofing behavior of polypropylene were employed, is given by way of comparison:

The following materials were mixed dry in the Turbula:
(i) 6,270 g of polypropylene;
(ii) 2,800 g of decabromobiphenyl;
(iii) 930 g of Sb$_2$O$_3$.

This mixture was charged into a Buss blender model PR 46.

The subsequent processing was as in Example 17.

The results obtained are reported in Table A.

TABLE A

| FORMULATIONS | \multicolumn{17}{c}{EXAMPLES} |
|---|---|---|---|---|---|---|---|---|---|---|---|---|---|---|---|---|---|
| | 10 | 11 | 12 | 13 | 14 | 15 | 16 | 17 | 18 | 19 | 20 | 21 | 22 | 23 | 24 | 25 | 26 |
| Polypropylene | 100 | 89.8 | 89.8 | 94.8 | 89.8 | 87.8 | 89.8 | 89.8 | 89.8 | 89.8 | 89.8 | 89.8 | 89.8 | 89.8 | 89.8 | 89.8 | 62.7 |
| Pharmaceutical liquid paraffin | | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | |
| $(NH_4)_3^{\oplus}(Sb_2Br_6)^{3\ominus}$ | | 10 | | | | | | | | | | | | | | | |
| $(NH_4)_3^{\oplus}(Sb_2Br_9)^{3\ominus}$ | | | 10 | | | | | | | | | | | | | | |
| $(NH_4)_7^{\oplus}(Sb_3Br_{16})^{7\ominus}$ | | | | 5 | 10 | 12 | | | | | | | | | | | |
| $(NH_4)_2^{\oplus}(BiBr_5)^{2\ominus}$ | | | | | | | 10 | | | | | | | | | | |
| Bis(melaminium) penta-bromoantimonate(III) | | | | | | | | 10 | | | | | | | | | |
| Bis(piperidinium) penta-bromoantimonate(III) | | | | | | | | | 10 | | | | | | | | |
| Bis(piperidinium) penta-chloroantimonate(III) | | | | | | | | | | 10 | | | | | | | |
| Bis(anilinium) penta-bromoantimonate(III) | | | | | | | | | | | 10 | | | | | | |
| Piperazinium penta-bromoantimonate(III) | | | | | | | | | | | | 10 | | | | | |

| FORMULATIONS | \multicolumn{17}{c}{EXAMPLES} |
|---|---|---|---|---|---|---|---|---|---|---|---|---|---|---|---|---|---|
| | 10 | 11 | 12 | 13 | 14 | 15 | 16 | 17 | 18 | 19 | 20 | 21 | 22 | 23 | 24 | 25 | 26 |
| 1-(2-Ammonioethyl)-piperazinium pentabromoantimonate (III) | | | | | | | | | | | | | 10 | | | | |
| 1-Tris(2-ammonioethyl)piperazinium-dodecabromo-diantimonate(III) | | | | | | | | | | | | | | 10 | | | |
| 1,2-Diammonioethane pentabromoantimonate (III) | | | | | | | | | | | | | | | 10 | | |
| Tris(piperazinium) dodecabromodi-bismuthate (III) | | | | | | | | | | | | | | | | 10 | |
| Decabromobiphenyl | | | | | | | | | | | | | | | | | 28 |
| $Sb_2O_3$ | | | | | | | | | | | | | | | | | 9.3 |
| Oxygen index (%) | 17 | 25.4 | 25.2 | 22.8 | 26.5 | 25.8 | 25.8 | 25.5 | 27.4 | 22 | 25.7 | 26.7 | 28.4 | 28.3 | 26.8 | 26.1 | 27.7 |
| UL 94 test: classification | | | | | | | | | | | | | | | | | |
| Thickness 3.2 mm | NC | V2 | V2 | V2 | V0 | V0 | V2 | V2 | V2 | V2 | V2 | V2 | V2 | V0 | V2 | V2 | NC |
| Thickness 1.6 mm | NC | V2 | | V2 | V2 | V0 | V2 | | | | | | | V0 | | | |
| Izod impact (kJ/m²) | 3.64 | 3.3 | 3 | | 3.2 | | | | 30.2 | | | | | 3.11 | 3.5 | | 2.55 |

The superiority of the compounds according to the invention vis-a-vis those of the prior art employed in high proportions was clearly apparent. Indeed, amounts which were three times less provided a high level of fireproofing, while retaining a higher level of impact strength.

EXAMPLE 27

Granules of polyamide 11 having the following characteristics: solution visocisty=1.01, density=1.03, melting point=185° C., were extruded in a Buss blender model PR 46. The granules produced were injection-molded into standardized test specimens on which the UL 94 test and the measurement of the oxygen index were performed.

EXAMPLE 28

The following materials were mixed:
(i) 9,480 g of polyamide 11 granules having the same characteristics as in Example 27;
(ii) 20 g of a pharmaceutical grade liquid paraffin, and then, after a mixing time required to disperse the liquid paraffin;
(iii) 500 g of $(NH_4)_3^{\oplus}(SbBt_6)^{3\ominus}$ were added.

This mixture was charged into a Buss blender model PR 46.

The granules produced were injection-molded into standardized test specimens on which the UL 45 test and the measurement of the oxygen index were performed.

EXAMPLE 29

The procedure of Example 28 was repeated, except that the $(NH_4)_3^{\oplus}(SbBr_6)^{3\ominus}$ was replaced with the same amount by weight of $(NH_4)_3^{\oplus}(Sb_2Br_9)^{3\ominus}$.

EXAMPLE 30

The procedure of Example 28 was repeated, except that the $(NH_4)_3^{\oplus}(SbBr_6)^{3\ominus}$ was replaced with the same amount by weight of $(NH_4)_7^{\oplus}(Sb_3Br_{16})^{7\ominus}$.

EXAMPLE 31

The procedure of example 30 was repeated, but with a different amount of $(NH_4)_7^{\oplus}(Sb_3Br_{16})^{7\ominus}$.

EXAMPLES 32, 33 and 34

The procedure of Example 28 was repeated, except that the compound $(NH_4)_3^{\oplus}(SbBr_6)^{3\ominus}$ was replaced with the following compounds:

EXAMPLE 32 bis(melaminium) pentabromoantimonate(III);

EXAMPLE 33

1,2-diammonioethane pentabromoantimonate(III);

EXAMPLE 34 bis(piperidinium) pentabromoantimonate(III).

EXAMPLE 35

This example, in which commercial products currently employed to improve the flameproofing behavior of polyamide 11 were used, is given by way of comparison.

The following materials were mixed dry in the Turbula:
(i) 9550 g of PA 11;
(ii) 300 g of decabromobiphenyl;
(iii) 150 g of $Sb_2O_3$.

This mixture was charged into a Buss PR 46 blender. The subsequent processing was as in Example 27. The results are reported in Table B.

TABLE B

| FORMULATIONS | EXAMPLES | | | | | | | | |
|---|---|---|---|---|---|---|---|---|---|
| | 27 | 28 | 29 | 30 | 31 | 32 | 33 | 34 | 35 |
| Polyamide 11 | 100 | 94.8 | 94.8 | 94.8 | 96.8 | 94.8 | 94.8 | 94.8 | 95.5 |
| Pharmaceutical liquid paraffin | — | 0.2 | 0.2 | 0.2 | 0.2 | 0.2 | 0.2 | 0.2 | — |
| $(NH_4)_3^{\oplus}(Sb_2Br_6)^{3\ominus}$ | | 5 | | | | | | | |
| $(NH_4)_3^{\oplus}(Sb_2Br_9)^{3\ominus}$ | | | 5 | | | | | | |
| $(NH_4)_7^{\oplus}(Sb_3Br_{16})^{7\ominus}$ | | | | 5 | 3 | | | | |
| Bis(melaminium) pentabromoantimonate(III) | | | | | | 5 | | | |
| 1,2-Diammonioethane pentabromoantimonate(III) | | | | | | | 5 | | |
| Bis(piperidinium) pentabromoantimonate(III) | | | | | | | | 5 | |
| Decabromobiphenyl | | | | | | | | | 3 |
| $Sb_2O_3$ | | | | | | | | | 1.5 |
| Oxygen index (%) | 22.8 | 35.1 | 34.8 | 36.5 | 36.9 | 31.9 | 33.1 | 33.3 | 31.4 |
| UL 94 test: | | | | | | | | | |
| Thickness 3.2 mm classification | V2 | V0 | V0 | V0 | V0 | V0 | V0 | V0 | V2 |
| Thickness 1.6 mm classification | V2 | V0 | V0 | V0 | V0 | V0 | V0 | V0 | |

EXAMPLE 36

Granules of a low-density polyethylene having a density of 0.91 g/cm³ were extruded in a Buss blender, model PR 46.

The granules produced were injection-molded into standardized test specimens on which the UL 94 test and the measurement of the oxygen index were performed.

EXAMPLE 37

The following materials were mixed in the Turbula:
(i) 8,480 g of low-density polyethylene;
(ii) 20 g of a liquid paraffin;
(iii) 1,500 g of $(NH_4)_7^{\oplus}(Sb_3Br_{16})^{7\ominus}$.

This mixture was charged into a Buss blender model PR 46.

The granules produced were injection-molded into standardized test specimens on which the UL 94 and the measurement of the oxygen index were performed.

EXAMPLES 38 and 39

The above procedure was repeated, except that the synthetic resin was an ethylene-vinyl acetate copolymer.

EXAMPLES 40 and 41

The above procedure was repeated, except that the synthetic resin was a polybutylene terephthalate.

EXAMPLES 42 and 43

The above procedure was repeated, except that the synthetic resin was an ABS resin.

The results of Examples 36 to 43 are reported in Table C.

TABLE C

| FORMULATIONS | EXAMPLES | | | | |
|---|---|---|---|---|---|
| | 36 | 37 | 38 | 39 | 40 |
| Low-density polyethylene | 100 | 84.8 | | | |
| Ethylene-vinyl acetate copolymer | | | 100 | 87.3 | |
| Polybutylene terephthalate | | | | | 100 |
| ABS resin | | | | | |
| $(NH_4)_7^{\oplus}(Sb_3Br_{16})^{7\ominus}$ | | 15 | | | |
| $(NH_4)_2^{\oplus}(BiBr_5)^{2\ominus}$ | | | | 12.5 | |
| Pharmaceutical liquid paraffin | | 0.2 | | 0.2 | |
| Oxygen index (%) | 18 | 24.9 | 21.1 | 24.2 | 21.6 |
| UL 94 test: | | | | | |
| Thickness 3.2 mm classification | NC | V2 | NC | NC | NC |
| Thickness 1.6 mm classification | | V2 | | | |

| FORMULATIONS | EXAMPLES | | |
|---|---|---|---|
| | 41 | 42 | 43 |
| Low-density polyethylene | | | |
| Ethylene-vinyl acetate copolymer | | | |
| Polybutylene terephthalate | 89.8 | | |
| ABS resin | | 100 | 89.8 |
| $(NH_4)_7^{\oplus}(Sb_3Br_{16})^{7\ominus}$ | 10 | | 10 |
| $(NH_4)_2^{\oplus}(BiBr_5)^{2\ominus}$ | | | |
| Pharmaceutical liquid paraffin | 0.2 | | 0.2 |
| Oxygen index (%) | 31.4 | 19.7 | 21.5 |
| UL 94 test: | | | |
| Thickness 3.2 mm classification | V0 | NC | NC |
| Thickness 1.6 mm classification | V0 | | |

EXAMPLE 44

The following materials were mixed (Turbula mixer):
(i) 8,680 g of polypropylene granules;
(ii) 20 g of a liquid paraffin, pharmaceutical grade;
(iii) 1,300 g of tetrabutylammonium tetrabromoantimonate(III): $[(nBu)_4N]^{\oplus}(SbBr_4)^{\ominus}$.

This mixture was charged into a Buss blender model FR 46 in which the average temperature was 200° C.

The granules produced were injection-molded into standardized test specimens on which UL 94 test and the measurement of the oxygen index were performed.

EXAMPLE 45

The procedure of Example 44 was repeated, except that a different amount of tetrabutylammonium tetrabromoantimonate(III) was employed.

The results obtained are reported in Table D.

TABLE D

| FORMULATIONS | EXAMPLES | |
|---|---|---|
| | 44 | 45 |
| Polypropylene | 86.80 | 83.20 |
| Pharmaceutical liquid paraffin | 0.20 | 0.20 |
| (nBu)$_4$ N$^\oplus$(SbBr$_4$)$^\ominus$ | 13 | 16.60 |
| Oxygen index (%) | 27.3 | 27.6 |
| UL 94 test: | | |
| Thickness 3.2 mm | V2 | V2 |
| Thickness 1.6 mm | V2 | V2 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter comprising an organic synthetic resin and, as a flame retardant therefor, an effective flameproofing amount of a nitrogenous/halometallic compound having the following general formula (I):

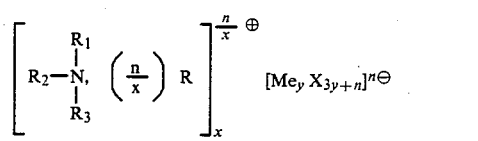

in which R, R$_1$, R$_2$ and R$_3$, which may be identical or different, are each a hydrogen atom, a linear or branched chain aliphatic hydrocarbon radical optionally substituted by one or more halogen atoms and containing up to 12 carbon atoms, a cycloaliphatic radical, or a phenyl radical or phenyl radical substituted by one or more halogen atoms, amino groups, or linear or branched chain aliphatic radicals containing up to 6 carbon atoms, with the proviso that R$_1$, R$_2$ and R$_3$ may together form, with the nitrogen atom from which they depend, an aromatic heterocyclic ring member, or substituted such ring member bearing one or more linear or branched chain aliphatic radicals containing up to 6 carbon atoms or halogen atom substituents, with the further proviso that R$_2$ and R$_3$ may together form, with the nitrogen atom from which they depend and a divalent radical (Y), a heterocyclic ring member containing from 2 to 10 carbon atoms and having the formula:

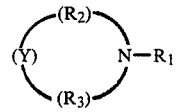

wherein (Y) is a valence bond, >N—H, —O—, —S—,

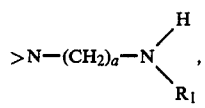

with a ranging from 2 to 6, and R$_1$ is as defined above, with the further proviso that R$_3$ may itself be a nitrogenous heterocyclic ring member, or substituted such heterocycle bearing one or more halogen atom, amino group, linear or branched chain aliphatic radical containing up to 10 carbon atoms, phenyl radical or amino residue substituents of the formula:

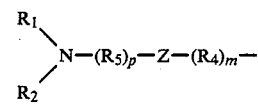

wherein R$_1$ and R$_2$ are as defined above, and R$_4$ and R$_5$, which may be identical or different, are each a divalent nitrogenous heterocyclic radical or a methylene radical, Z is a single valence bond or a divalent radical selected from among the following:

—NH—(CH$_2$)—$_b$NH—, with b ranging from 0 to 6, —(CH$_2$)—$_c$, with c ranging from 1 to 6, and

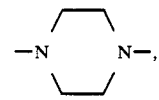

and p and m range from 1 to 6; Me is a metal; X is a halogen atom; and x, y and n are integers ranging from 1 to 10, with n≧x.

2. The composition as defined by claim 1, wherein the formula (I), R, R$_1$, R$_2$ and R$_3$ are hydrogen atoms, Me is arsenic, antimony(III) or bismuth(III), and X is bromine or chlorine.

3. The composition as defined by claim 1, said compound of formula (I) comprising triammonium hexabromoantimonate(III), triammonium nonabromodiantimonate(III), heptaammonium hexadecabromotriantimonate(III), triammonium nonabromodibismuthate(III) or triammonium nonachlorodiantimonate(III).

4. The composition as defined by claim 1, wherein formula (I), R, R$_1$ and R$_2$ are hydrogen atoms, R$_3$ is a linear or branched chain aliphatic hydrocarbon radical containing up to 12 carbon atoms, a cyclohexane-containing radical or a phenyl radical; Me is antimony(III) or bismuth(III) and X is bromine or chlorine.

5. The composition as defined by claim 1, said compound of formula (I) comprising bis(n-butylammonium) pentabromoantimonate(III), bis(isobutylammonium) pentabromoantimonate(III), bis(tri-n-butylammonium) pentabromoantimonate(III), bis(anilinium) pentabromoantimonate(III) or bis(cyclohexylammonium) pentabromoantimonate(III).

6. The composition as defined by claim 1, wherein formula (I), R is a hydrogen atom, $R_1$, $R_2$ and $R_3$ together form, with the nitrogen atom from which they depend, an aromatic heterocyclic ring member, or substituted such heterocycle bearing one or more linear aliphatic radical substituents containing up to 3 carbon atoms or halogen atoms; Me is antimony(III) or bismuth(III) and X is bromine or chlorine.

7. The composition as defined by claim 1, wherein formula (I), R and $R_1$ are hydrogen atoms, $R_2$ and $R_3$ together form, with the nitrogen atom from which they depend and a divalent radical (Y), a heterocyclic ring member containing from 2 to 6 carbon atoms, having the structure:

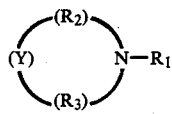

in which (Y) is a valence bond, $>N-H$ or $>N-(CH_2)-NH_2$; Me is antimony(III) or bismuth(III) and X is bromine or chlorine.

8. The composition as defined by claim 1, said compound of formula (I) comprising bis(piperidinium) pentabromoantimonate(III), piperazinium pentabromoantimonate(III), piperazinium pentabromobismuthate(III), 1-(2-ammonioethyl)piperazinium pentabromoantimonate(III) or 1-tris(2-ammonioethyl)piperazinium dodecabromodiantimonate(III).

9. The composition as defined by claim 1, wherein formula (I), R, $R_1$ and $R_2$ are hydrogen atoms, $R_3$ is a nitrogenous heterocyclic radical, or substituted such heterocycle bearing one or more amino group substituents, linear or branched chain aliphatic hydrocarbyl radicals containing up to 10 carbon atoms or phenyl radicals; Me is antimony(III) or bismuth(III) and X is bromine or chlorine.

10. The composition as defined by claim 9, wherein formula (I), $R_3$ is an s-triazine, 1,3-diazine, 1,2,4-triazolyl, benzimidazolyl or phthalimide radical.

11. The composition as defined by claim 10, said compound of formula (I) comprising bis(melaminium) pentabromoantimonate(III).

12. The composition as defined by claim 1, wherein formula (I), R, $R_1$ and $R_2$ are hydrogen atoms, $R_3$ is an amino radical of the formula $H_2N-(R_5)_p-Z-(R_4)_m-$ in which $R_4$ and $R_5$ are methylene residues or a divalent s-triazine radical, Z is a single valence bond or a divalent radical of the formula:

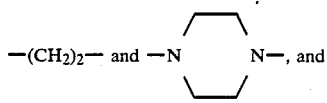

p and m are numbers ranging from 1 to 4; Me is antimony(III) or bismuth(III) and X is bromine or chlorine.

13. The composition as defined by claim 12, wherein formula (I), $R_3$ is an amino radical of the formula $H_2N(CH_2)_p-Z(CH_2)_m-$ in which Z is a single valence bond or the divalent radical $>N-H$ and m=p and is a member ranging from 1 to 3.

14. The composition as defined by claim 13, said compound of formula (I) comprising 1,2-diammonioethane pentabromoantimonate(III) or bis(2-ammonioethyl)ammonium hexabromoantimonate(III).

15. A nitrogenous/halometallic compound having the following general formula (I-a):

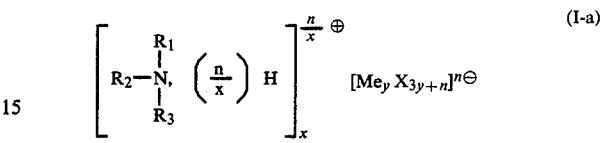

in which $R_1$ and $R_2$, which may be identical or different, are each a hydrogen atom, a linear or branched chain aliphatic hydrocarbon radical containing up to 12 carbon atoms or a phenyl radical; $R_3$ is a nitrogenous heterocyclic radical, or a C-substituted such heterocycle bearing one or more halogen atom, amino group, or linear or branched chain aliphatic radical substituents containing up to 10 carbon atoms, or phenyl radicals or amino residues of the formula $H_2N-(R_5)_p-Z(R_4)_m-$ in which $R_4$ and $R_5$, which may be identical or different, are each divalent heterocyclic radicals, Z is a divalent radical selected from among the following:

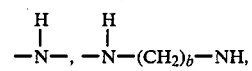

with b ranging from 0 to 6,

or a $-(CH_2)-_c$ radical, with c ranging from 1 to 6, when $R_5$ and $R_4$ are divalent heterocyclic radicals, and p and m range from 1 to 6, with the proviso that $R_2$ and $R_3$ may together form, with the nitrogen atom from which they depend and a divalent radical $>N-H$ or $>N-(CH_2)_a-NH_2$, with a ranging from 2 to 6, a heterocyclic ring member containing from 2 to 10 carbon atoms; Me is arsenic, antimony (III) or bismuth (III); X is a halogen atom; and x, y and n are integers ranging from 1 to 10, with $n \geq x$.

16. The compound as defined by claim 15, wherein formula (I-a), $R_1$ and $R_2$ are hydrogen atoms; Me is bismuth or antimony, X is bromine or chlorine, and $R_3$ is an s-triazine, 1,3-diazine, 1,2,4-triazolyl, benzimidazolyl or phthalimide radical.

17. The compound as defined by claim 15, the same being bis(melaminium) pentabromoantimonate(III).

18. The compound as defined by claim 15, the same being bis(benzoguanidinium) pentabromoantimonate(III).

19. The compound as defined by claim 15, the same being tris(3-ammonio-1,2,4-triazole) hexabromoantimonate(III).

20. The compound as defined by claim 15, wherein formula (I-a), $R_1$ is a hydrogen atom, and $R_2$ and $R_3$ together form, with the nitrogen atom from which they depend and an >N—H or >N—(CH₂)₂ radical, a piperazine heterocycle.

21. The compound as defined by claim 15, the same being piperazinium pentabromoantimonate(III).

22. The compound as defined by claim 15, the same being tris(piperazinium) dodecabromodibismuthate(III).

23. The compound as defined by claim 15, the same being 1-(2-ammonioethyl)piperazinium pentabromoantimonate(III).

24. The compound as defined by claim 15, the same being 1-tris(2-ammonioethyl)piperazinium dodecabromodiantimonate(III).

25. The composition as defined by claim 1, comprising from 1% to 18% by weight of said compound of formula (I).

26. The composition as defined by claim 1, wherein formula (I), Me is arsenic(III), antimony(III) or bismuth(III).

27. A shaped article comprising the composition of matter as defined by claim 1.

* * * * *